US011416591B2

(12) United States Patent
Sakumoto et al.

(10) Patent No.: US 11,416,591 B2
(45) Date of Patent: Aug. 16, 2022

(54) ELECTRONIC APPARATUS, AUTHENTICATION METHOD, AND PROGRAM (71) Applicant: SONY CORPORATION, Tokyo (JP)

(72) Inventors: Koichi Sakumoto, Tokyo (JP); Atsushi Okubo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1063 days.

(21) Appl. No.: 16/071,269

(22) PCT Filed: Feb. 2, 2017

(86) PCT No.: PCT/JP2017/003806
§ 371 (c)(1),
(2) Date: Jul. 19, 2018

(87) PCT Pub. No.: WO2017/159101
PCT Pub. Date: Sep. 21, 2017

(65) Prior Publication Data
US 2021/0200842 A1 Jul. 1, 2021

(30) Foreign Application Priority Data
Mar. 15, 2016 (JP) .............. JP2016-051030

(51) Int. Cl.
G06F 21/32 (2013.01)
G06F 1/16 (2006.01)
(Continued)

(52) U.S. Cl.
CPC .............. *G06F 21/32* (2013.01); *G06F 1/163* (2013.01); *G06F 1/3231* (2013.01);
(Continued)

(58) Field of Classification Search
CPC ........ G06F 21/32; G06F 1/163; G06F 1/3231; G06F 21/44; G06V 40/1365;
(Continued)

(56) References Cited

U.S. PATENT DOCUMENTS 9,135,495 B1 9/2015 Pope et al.
2008/0216171 A1 9/2008 Sano et al.
(Continued)

FOREIGN PATENT DOCUMENTS

CN 101246532 A 8/2008
CN 101620657 A 1/2010
(Continued)

OTHER PUBLICATIONS

Apr. 28, 2020, Japanese Office Action issued for related JP application No. 2018-505327.

(Continued)

Primary Examiner — Abhishek Sarma
(74) Attorney, Agent, or Firm — Paratus Law Group, PLLC (57) ABSTRACT There is provided an electronic apparatus, and an improved design flexibility and minimized power consumption for biometric authentication in an electronic apparatus that performs biometric authentication, the electronic apparatus including: a wearable part movable to be worn on a user's body; and a biometric information acquisition unit provided on the wearable part and configured to acquire biometric information of the user for user authentication. This configuration makes it possible to improve design flexibility and minimize power consumption for biometric authentication in an electronic apparatus that performs biometric authentication.

16 Claims, 7 Drawing Sheets (51) Int. Cl.
*G06F 1/3231* (2019.01)
*G06V 40/70* (2022.01)
*G06V 40/18* (2022.01)
*G06V 40/12* (2022.01)
*G06V 40/14* (2022.01)

(52) U.S. Cl.
CPC ........ G06V 40/1365 (2022.01); G06V 40/197 (2022.01); G06V 40/70 (2022.01); G06V 40/14 (2022.01)

(58) Field of Classification Search
CPC ...... G06V 40/197; G06V 40/70; G06V 40/14; G06V 40/12; A61B 2560/0209; A61B 5/681; A61B 5/1172
See application file for complete search history.

(56) References Cited

U.S. PATENT DOCUMENTS

| | | |
|---|---|---|
| 2014/0126782 A1 | 5/2014 | Takai et al. |
| 2015/0031333 A1 | 1/2015 | Lee |
| 2015/0161371 A1 | 6/2015 | Hoshi et al. |
| 2016/0364560 A1 | 12/2016 | Yan |
| 2017/0017785 A1* | 1/2017 | Rice .................. G06K 9/00906 |

FOREIGN PATENT DOCUMENTS

| | | |
|---|---|---|
| CN | 104506315 A | 4/2015 |
| CN | 105117625 A | 12/2015 |
| JP | 2000-181870 A | 6/2000 |
| JP | 2002-312324 A | 10/2002 |
| JP | 2007-330503 A | 12/2007 |
| JP | 2008-198028 A | 8/2008 |
| JP | 2010-009513 A | 1/2010 |
| JP | 2014-143568 A | 8/2014 |
| JP | 2015-055952 A | 3/2015 |
| JP | 2015-094961 A | 5/2015 |

OTHER PUBLICATIONS

Feb. 27, 2019, European Search Report issued for related EP Application No. 17766109.7.

* cited by examiner

ELECTRONIC APPARATUS, AUTHENTICATION METHOD, AND PROGRAM

CROSS REFERENCE TO PRIOR APPLICATION

This application is a National Stage Patent Application of PCT International Patent Application No. PCT/JP2017/003806 (filed on Feb. 2, 2017) under 35 U.S.C. §371, which claims priority to Japanese Patent Application No. 2016-051030 (filed on Mar. 15, 2016), which are all hereby incorporated by reference in their entirety.

TECHNICAL FIELD

The present disclosure relates to an electronic apparatus, an authentication method, and a program.

BACKGROUND ART

Conventionally, Patent Literature 1 below describes an apparatus including a button that functions as a normal button when the button is pressed, in which fingerprint sensing is performed when the button surface is touched.

CITATION LIST

Patent Literature

Patent Literature 1: U.S. Pat. No. 9,135,495B

DISCLOSURE OF INVENTION

Technical Problem

However, the technology described in Patent Literature 1 has a problem in that the button needs to be disposed on the same surface as a fingerprint sensor, which causes a decrease in design flexibility. Particularly in a wearable device of a watch type, a glasses type, or the like, it is desirable that surface unevenness due to button installation be avoided, because design is of importance.

In addition, power consumption increases if fingerprint sensing is always performed; particularly in a wearable device of a watch type, a glasses type, or the like, which is limited in battery capacity, power consumption is required to be reduced.

Hence, it has been required that, in an electronic apparatus that performs biometric authentication, design flexibility be improved and power consumption for biometric authentication be minimized.

Solution to Problem

According to the present disclosure, there is provided an electronic apparatus and an electronic apparatus including: a wearable part movable to be worn on a user's body; and a biometric information acquisition unit provided on the wearable part and configured to acquire biometric information of the user for user authentication.

In addition, according to the present disclosure, there is provided an electronic apparatus including: a wearable part movable to be worn on or detached from a user's body; a biometric information acquisition unit configured to acquire biometric information of the user for user authentication; and a detection unit configured to detect movement of the wearable part. The biometric information acquisition unit acquires the biometric information when the detection unit detects that the wearable part is worn on the user's body.

In addition, according to the present disclosure, there is provided an authentication method including: detecting movement of a wearable part movable for an electronic apparatus to be worn on a user's body; and acquiring biometric information of the user in order to perform authentication on a basis of the biometric information when the movement of the wearable part is detected.

In addition, according to the present disclosure, there is provided a program causing a computer to function as: means for detecting movement of a wearable part movable for an electronic apparatus to be worn on a user's body; and means for acquiring biometric information of the user in order to perform authentication on a basis of the biometric information when the movement of the wearable part is detected.

Advantageous Effects of Invention

As described above, according to the present disclosure, in an electronic apparatus that performs biometric authentication, design flexibility can be improved and power consumption for biometric authentication can be minimized.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Figure 1:
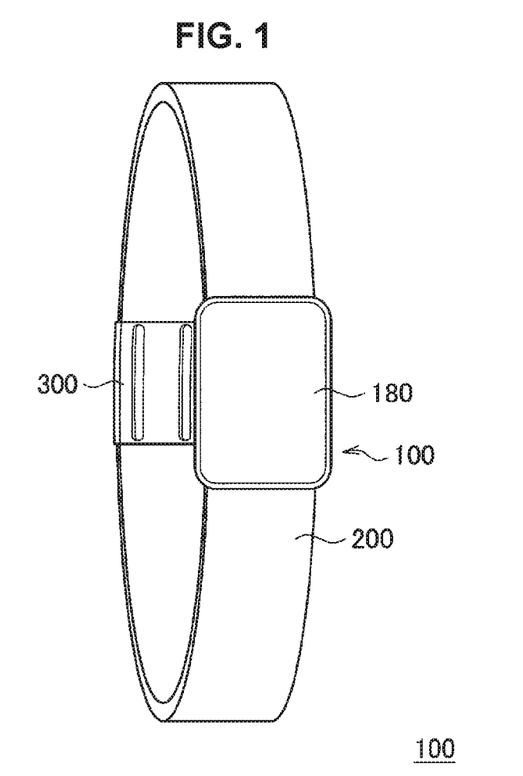
FIG. 1 is a schematic diagram illustrating a schematic configuration of an electronic apparatus according to an embodiment of the present disclosure.

Note that description is given in the following order.
1. Configuration example of appearance of electronic apparatus
2. Authentication mode of electronic apparatus
3. Example in which belt includes leather belt
4. Block configuration example of electronic apparatus
5. Method for associating fingerprint sensor with control unit
6. Example of application to glasses-type device 1. Configuration Example of Appearance of Electronic Apparatus First, a schematic configuration of an electronic apparatus 1000 according to an embodiment of the present disclosure is described with reference to FIG. 1. As illustrated in FIG. 1, the electronic apparatus 1000 is configured as a watch-type wearable device. The electronic apparatus 1000 includes a main body 100, and a belt 200 and a buckle (wearable part) 300 configured to be worn on a user's arm. The main body 100 is provided with a display unit 180. The user of the electronic apparatus 1000 can wear the electronic apparatus 1000 on the arm by putting the arm through the belt 200 of the electronic apparatus 1000 and fastening the buckle 300. After that, by performing predetermined authentication processing, the user can obtain available service via the electronic apparatus 1000. Examples of available service include e-mail. SNS, electronic cash, a key function such as Smart Lock, Wi-Fi/4G, and the like.

The display unit 180 has a touch sensor provided on its surface and thus functions as a touch panel. By touching the display unit 180, the user can input operation information to the electronic apparatus 1000 and use the various types of service mentioned above.

Figure 2:
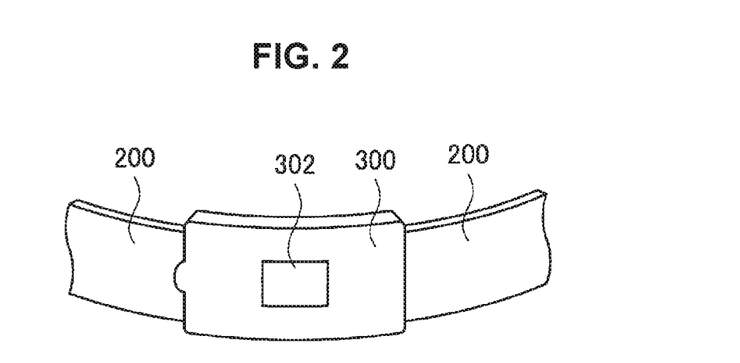
FIG. 2 is a schematic diagram illustrating a front side of a buckle.

FIG. 2 is a schematic diagram illustrating a front side of the buckle 300. As illustrated in FIG. 2, the buckle 300 of the electronic apparatus 1000 is provided with a fingerprint sensor (biometric information acquisition unit) 302. The fingerprint sensor 302 authenticates the user's fingerprint by a scheme such as an optical scheme of acquiring a fingerprint image by an image sensor such as a CCD or a CMOS, a capacitive scheme of reading a fingerprint by utilizing occurrence of a difference in capacitance due to a difference in a distance from the skin of a finger to a semiconductor surface between a peak and a valley, an electrolysis intensity measurement scheme of reading a fingerprint by utilizing occurrence of a difference in field intensity due to a difference in a distance from the dermis to a semiconductor surface between a peak and a valley when an electromagnetic wave caused to enter a finger from an exposed electrode of a sensor propagates through the dermis having high conductivity to be emitted from the finger surface, a pressure-sensing scheme of reading unevenness of grooves of a fingerprint by pressure, or a heat-sensing scheme of reading unevenness of grooves of a fingerprint by temperature. The fingerprint sensor 302 is provided on a front surface of the buckle 300, at a place that the user presses with a finger when fastening the buckle 300. Note that the fingerprint sensor 302 may be provided on the belt 200 or the main body 100. In addition, a sensor that acquires other biometric information of the user may be provided instead of the fingerprint sensor 302; for example, a sensor that acquires vein information of the user's hand, a sensor that acquires information of the user's voice (voice print), or the like may be provided.

Figure 3:
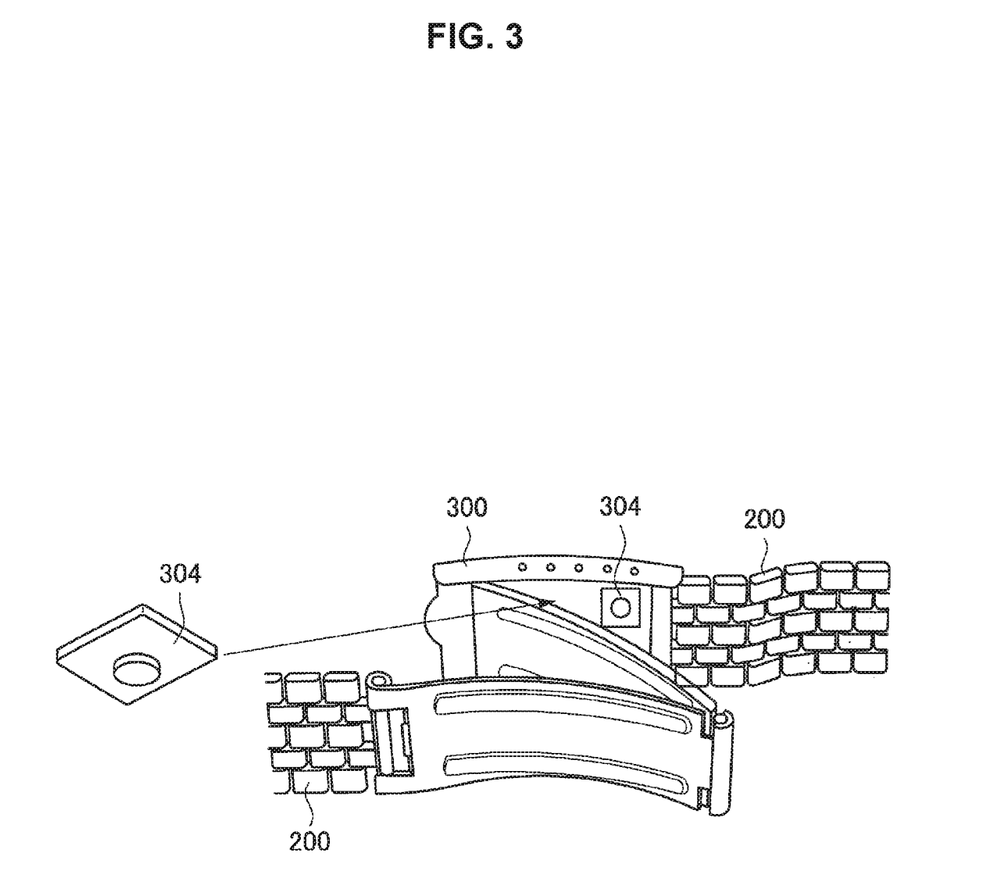
FIG. 3 is a schematic diagram illustrating a buckle in back view.

FIG. 3 is a schematic diagram illustrating the buckle 300 in back view. As illustrated in FIG. 2, a back surface of the buckle 300 is provided with a push switch (detection unit) 304. When the user fastens (closes) the buckle 300, the push switch 304 is pressed, and the push switch 304 enters an on (ON) state. On the other hand, when the user opens the buckle 300, the push switch 304 enters an off (OFF) state.

2. Authentication Mode of Electronic Apparatus

Figure 4:
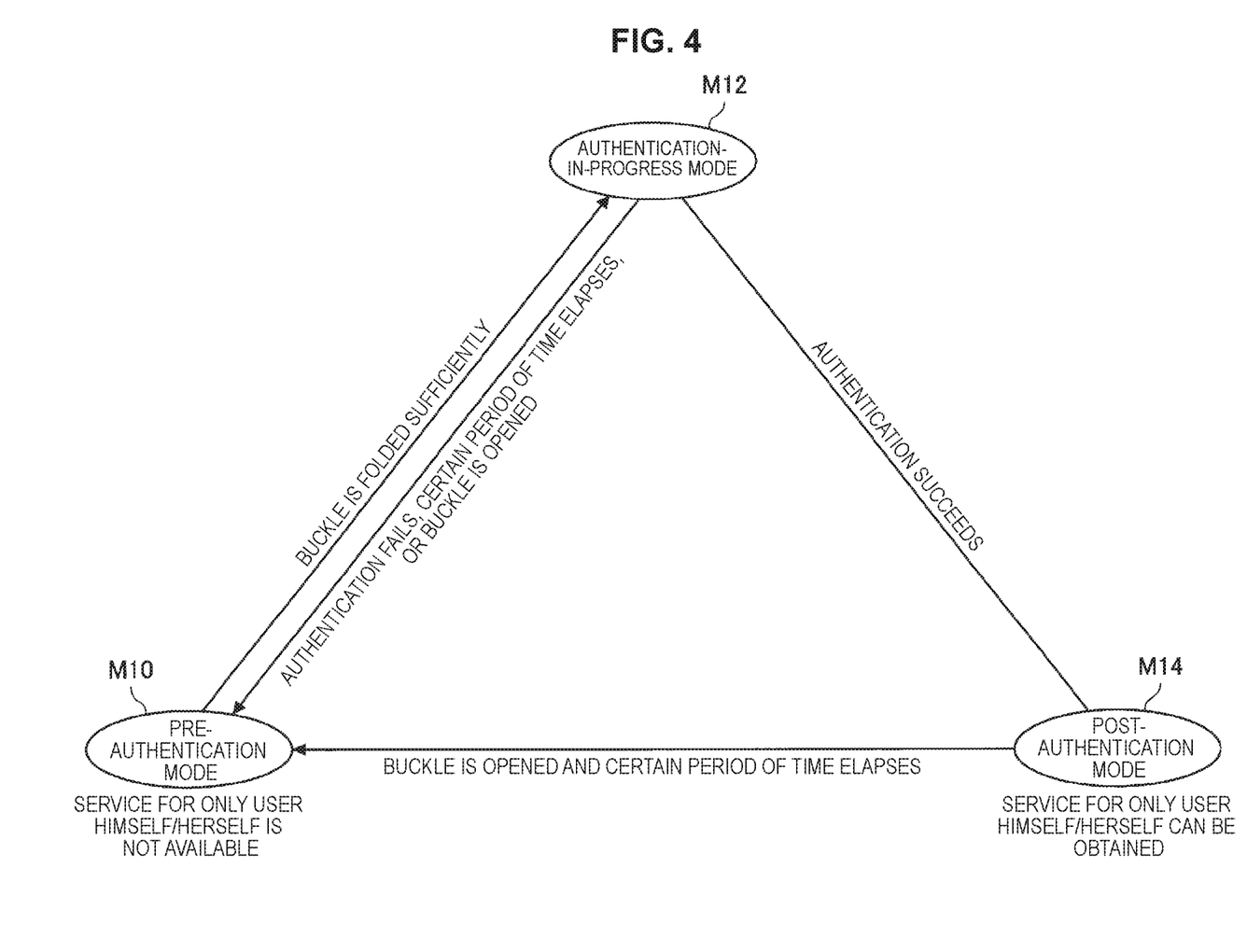
FIG. 4 is a schematic diagram illustrating an authentication mode of an electronic apparatus.

FIG. 4 is a schematic diagram illustrating an authentication mode of the electronic apparatus 1000. The mode before the user wears the electronic apparatus 1000 on the arm is a pre-authentication mode M10, in which service available to the user himself/herself is not available. When the user wears the electronic apparatus 1000 on the arm and folds the buckle 300 sufficiently, the push switch 304 enters an on state and the mode transitions to an authentication-in-progress mode M12. When the mode transitions to the authentication-in-progress mode M12, the fingerprint sensor 302 starts sensing. Thus, authentication using the fingerprint of the user's finger is performed.

When fingerprint authentication succeeds, the mode transitions to a post-authentication mode M14. The post-authentication mode is a state in which service available to only the user himself/herself can be obtained. In the post-authentication mode M14, the user himself/herself who has performed authentication is authorized as a legitimate user, and service available to the user himself/herself can be obtained. In addition, when the mode transitions to the post-authentication mode M14, the fingerprint sensor 302 is turned off (OFF). The post-authentication mode M14 basically continues until the user opens the buckle 300. In the post-authentication mode M14, when the buckle 300 is opened and the push switch 304 is turned off, the mode transitions to the pre-authentication mode M10 after elapse of a certain period of time.

The authentication-in-progress mode M12 is set for only a predetermined period of time after the push switch 304 enters an on state. In the case where fingerprint authentication does not succeed during this predetermined period of time, the mode returns to the pre-authentication mode M10. In addition, the mode returns to the pre-authentication mode also in the case where the buckle 300 is opened and the push switch 304 is turned off during this predetermined period of time.

As described above, according to the present embodiment, the fingerprint sensor 302 is turned on when the buckle 300 is fastened and the push switch 304 is turned on, and the fingerprint sensor 302 is turned off when the buckle 300 is opened and the push switch 304 is turned off. In addition, the fingerprint sensor 302 is on for only a predetermined period of time after the buckle 300 is fastened and the push switch 304 is turned on. Therefore, the fingerprint sensor 302 is not always on; thus, power consumption can be significantly reduced.

In addition, since the fingerprint sensor 302 is provided at a place that the user presses with a finger when fastening the buckle 300, fingerprint authentication can be performed at the same time as the user fastens the buckle 300 and the fingerprint sensor 302 is turned on.

In addition, since the push switch 304 that switches on/off of the fingerprint sensor 302 is disposed on the hack side of the buckle 300, the push switch 304 is not disposed on the front side of the buckle 300 or the front side of the electronic apparatus 1000. This can improve design flexibility of the electronic apparatus 1000, and can minimize limitations in design.

Note that lighting, display, or the like may be performed on the display unit 180 by an LED, an LCD, or the like to make the user aware that the fingerprint sensor 302 is on during the authentication-in-progress mode M12.

Figure 5:
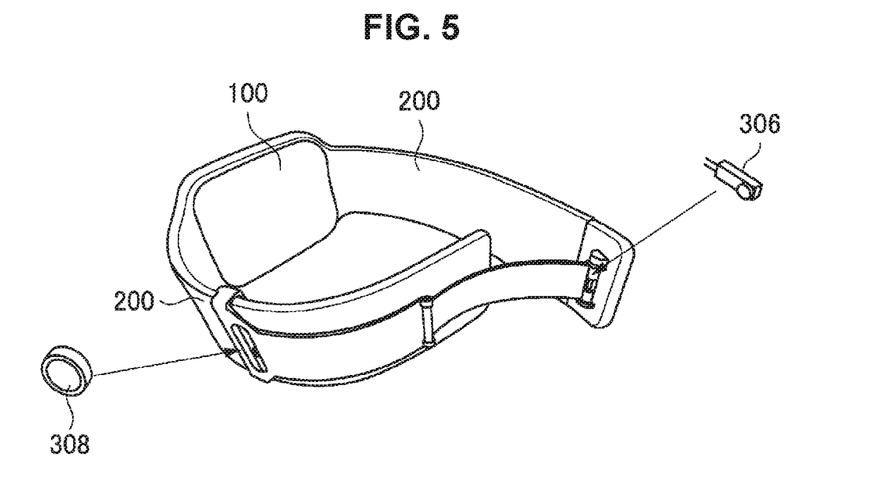
FIG. 5 is a schematic diagram illustrating an example in which a magnetic proximity sensor is used instead of a push switch.

In addition, although the push switch 304 is exemplified as a switch that switches on/off of the fingerprint sensor 302, a magnetic proximity sensor 306 illustrated in FIG. 5 may be used. In the example illustrated in FIG. 5, the magnetic proximity sensor 306 and a magnet 308 are disposed on the hack side of the buckle 300, and when the buckle 300 is fastened, the magnetic proximity sensor 306 and the magnet 308 come close to each other and the magnetic proximity sensor 306 detects magnetism of the magnet 308. Then, on detecting magnetism of the magnet 308, the magnetic proximity sensor 306 turns on the fingerprint sensor 302.

Figure 6:
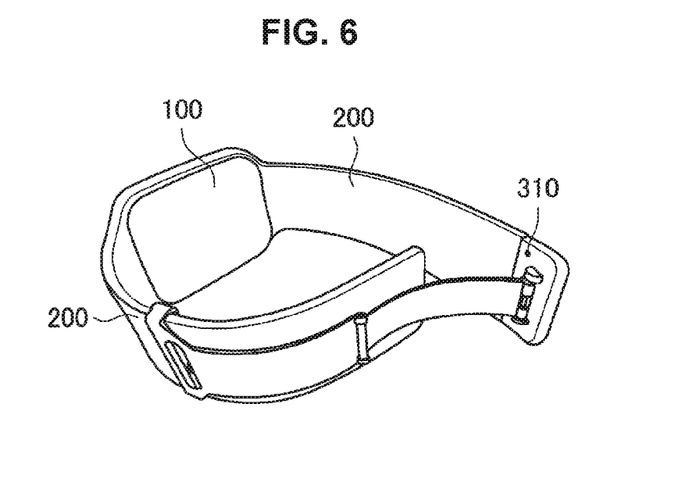
FIG. 6 is a schematic diagram illustrating an example in which an illuminance sensor is used instead of a push switch.

In addition, as illustrated in FIG. 6, an illuminance sensor 310 may be disposed on the back side of the buckle 300, instead of the push switch 304, and the illuminance sensor may detect that the buckle 300 is fastened. When the buckle 300 is opened, the illuminance sensor 310 detects light to be turned on, and when the buckle 300 is closed, the illuminance sensor 310 does not detect light and is turned off; thus, the illuminance sensor 310 can detect whether or not the buckle is closed.

Note that a technique for detecting open/close of the buckle 300 is not limited to the above, as long as the fingerprint sensor 302 can be on for only a certain period of time after the buckle 300 is closed.

In addition, although there are various types of the buckle 300, the type is not particularly limited, as long as a switch such as the push switch 304 can detect that the buckle 300 is closed.

In addition, in the case where a long period of time such as 24 hours elapses, for example, in the post-authentication mode M14, the mode may be caused to transition to the pre-authentication mode M10.

In addition, the mode may be caused to transition to the authentication-in-progress mode M12 in response to a trigger other than the push switch 304 being turned on. For example, after fingerprint authentication succeeds when the electronic apparatus 1000 is worm, fingerprint authentication may be performed again for identity verification when an application or the like is purchased using the electronic apparatus 1000 on the Internet. In this case, transition to the authentication-in-progress mode M12 is performed by being triggered by indication of the intent to purchase an application or the like by user operation.

The transition to the authentication-in-progress mode M12 triggered by purchase of an application or the like is performed also from the pre-authentication mode M10. For example, in the case where the mode transitions from the pre-authentication mode M10 to the authentication-in-progress mode M12 and returns to the pre-authentication mode M10 because of failure of fingerprint authentication, elapse of a certain period of time, or the like, it is possible for the user to use only a watch function of the electronic apparatus 1000 in the pre-authentication mode M10. At this time, when the user tries to purchase an application or the like on the Internet, the mode transitions from the pre-authentication mode M10 to the authentication-in-progress mode M12 for identity verification; and fingerprint authentication for identity verification is performed. Note that these triggers other than the push switch 304 being turned on will be referred to as software triggers.

3. Example in which Belt Includes Leather Belt

Figure 7:
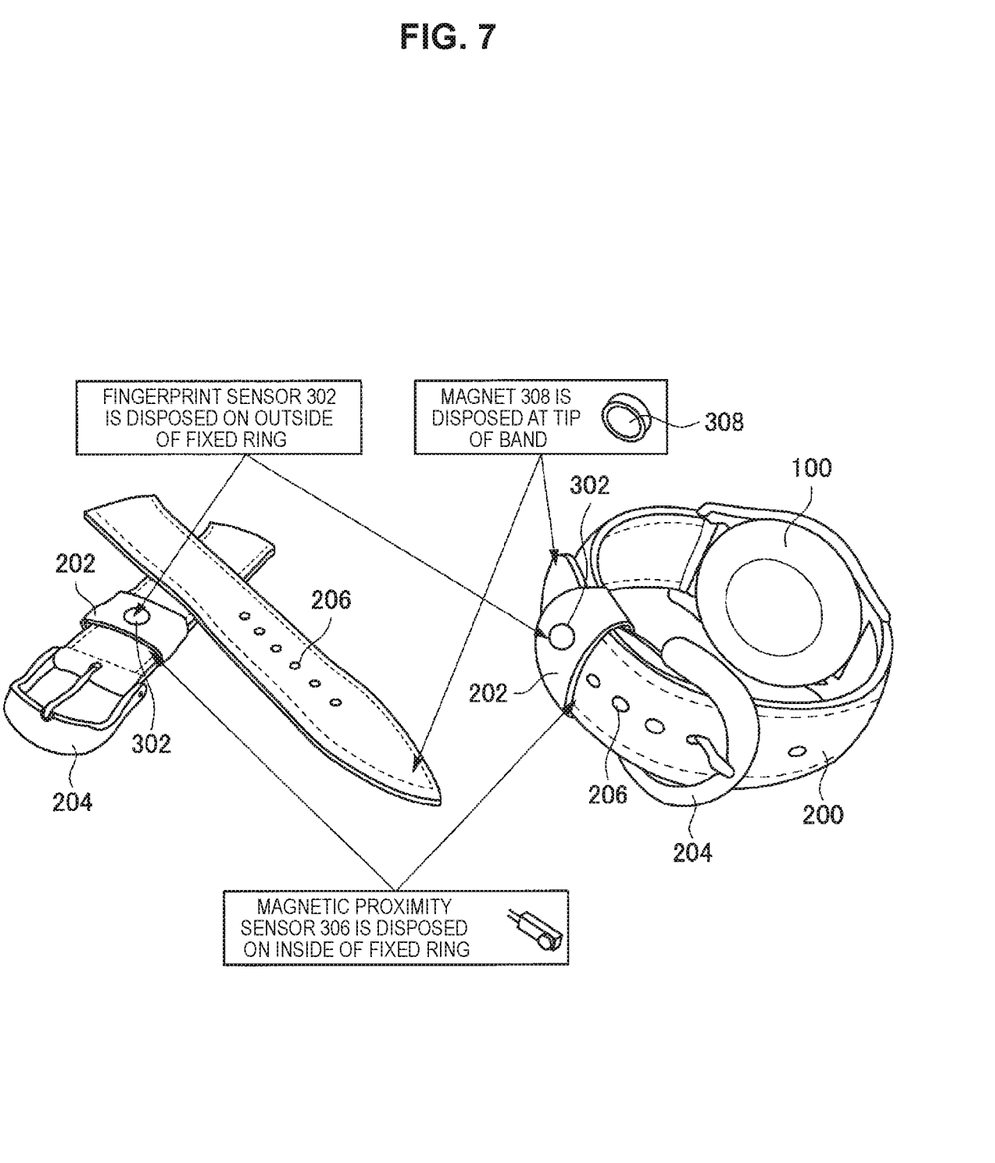
FIG. 7 is a schematic diagram illustrating a case where a belt includes a leather belt or the like, and an electronic apparatus is worn on a user's arm by a belt hole type instead of a buckle.

FIG. 7 is a schematic diagram illustrating a case where the belt 200 includes a leather belt or the like, and the electronic apparatus 1000 is worn on the user's arm by a belt hole type instead of the buckle 300. In the case of this type, the magnet 308 is disposed at a tip of the belt 200, and the magnetic proximity sensor 306 is disposed on the inside of a fixed ring (or a free ring 203) 202 into which the tip of the belt 200 is inserted. In addition, the fingerprint sensor 302 is disposed on the outside of the fixed ring 202. Note that in the case where the belt 200 is provided with the free ring side by side with the fixed ring 202, the magnetic proximity sensor 306 may be disposed on the inside of the free ring 203, and the fingerprint sensor 302 may be disposed on the outside of the free ring 203.

With the configuration illustrated in FIG. 7, when the tip of the belt 200 is inserted into the fixed ring 202 and the electronic apparatus 1000 is worn on the user's arm, the magnetic proximity sensor 306 detects magnetism of the magnet 308 and turns on the fingerprint sensor 302. Thus, transition from the pre-authentication mode M10 to the authentication-in-progress mode M12 is performed.

In addition, since the fingerprint sensor 302 is disposed on the outside of the fixed ring 202, the fingerprint of the user's finger touches the fixed ring 202 at the timing of insertion of the tip of the belt 200 into the fixed ring 202, so that fingerprint authentication can be performed.

In the configuration illustrated in FIG. 7, the fingerprint sensor 302 may be disposed on the outside of the belt 200 itself or a buckle 204, instead of the outside of the fixed ring 202. In addition, also the magnetic proximity sensor 306 may be disposed on the inside of the buckle 204, instead of the inside of the fixed ring 202. In addition, the magnet 308 may be disposed on the whole or part of the belt 200 or near a hole 206, instead of the tip of the belt 200.

Note that also in the configuration illustrated in FIG. 7, the push switch 340 may be used, instead of the magnetic proximity sensor 306, to detect that one end of the belt 200 is inserted into the fixed ring 202. In that case, the magnet 308 is unnecessary.

4. Block Configuration Example of Electronic Apparatus

Figure 8:
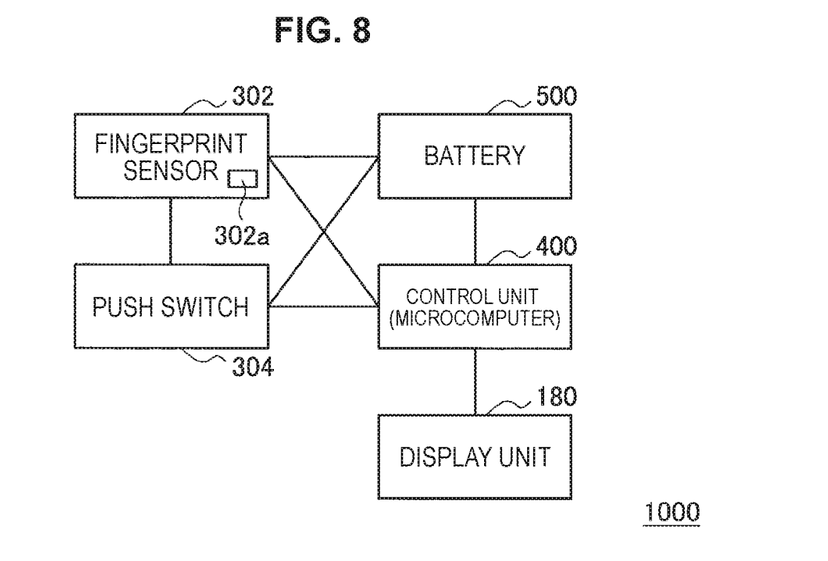
FIG. 8 is a block diagram illustrating a configuration of an electronic apparatus.

FIG. 8 is a block diagram illustrating a configuration of the electronic apparatus 1000. As illustrated in FIG. 6, the electronic apparatus 1000 includes the display unit 180, the fingerprint sensor 302, the push switch 304, a control unit (microcomputer) 400, and a battery 500. The display unit 180 and the control unit 400 are provided in the main body 100. In addition, the battery 500 is provided inside the main body 100, the belt 200, or the buckle 300.

When the user wears the electronic apparatus 1000 on the arm and fastens the buckle 300, the push switch 304 is turned on, and a signal (push switch on signal) indicating that is sent to the control unit 400. On receiving the push switch on signal, the control unit 400 turns on the fingerprint sensor 302. Thus, the mode transitions from the pre-authentication mode M10 to the authentication-in-progress mode M12, and the fingerprint sensor 302 starts sensing.

To perform fingerprint authentication, the electronic apparatus 1000 stores the user's fingerprint information in advance. The fingerprint information is stored in the fingerprint sensor 302 or the control unit 400, in the case where the fingerprint information is stored in the fingerprint sensor 302, the fingerprint information is stored in a microcomputer 302a included in the fingerprint sensor 302, in this case, the microcomputer 302a compares information of the user's fingerprint acquired by the fingerprint sensor 302 with the stored fingerprint information, determines success/failure of authentication, and sends authentication success/failure information indicating whether or not authentication is possible to the control unit 400.

On receiving the authentication success/failure information, on the basis of the authentication success/failure information, the control unit 400 causes the mode to transition from the authentication-in-progress mode M12 to the post-authentication mode M14 and enables service available to the user to be provided in the case where authentication has succeeded. On the other hand, the control unit 400 causes the mode to transition from the authentication-in-progress mode M12 to the pre-authentication mode M10 in the case where authentication has failed.

In addition, in the case where the fingerprint information is stored in the control unit 400, the fingerprint sensor 302 sends the acquired information of the user's fingerprint to the control unit 400. The control unit 400 acquires information of the user's fingerprint acquired by the fingerprint sensor 302. The control unit 400 compares information of the user's fingerprint acquired by the fingerprint sensor 302 with the stored fingerprint information, and determines success/failure of authentication. The control unit 400 causes the mode to transition from the authentication-in-progress mode M12 to the post-authentication mode M14 and enables service available to the user to be provided in the case where authentication has succeeded. On the other hand, the control unit 400 causes the mode to transition from the authentication-in-progress mode M12 to the pre-authentication mode M10 in the case where authentication has failed.

In addition, in the case of having caused the mode to transition from the authentication-in-progress mode M12 to the post-authentication mode M14, the control unit 400 turns off the fingerprint sensor 302. After that, in the case where a necessity to perform identity verification is caused by a software trigger, the control unit 400 turns on the fingerprint sensor 302 and performs fingerprint authentication again.

In addition, after turning on the fingerprint sensor 302 on the basis of the push switch on signal, the control unit 400 causes the mode to transition from the authentication-in-progress mode M12 to the pre-authentication mode M10 in the case where authentication does not succeed for a certain period of time. In addition, after turning on the fingerprint sensor 302 on the basis of the push switch on signal, the control unit 400 causes the mode to transition from the authentication-in-progress mode M12 to the pre-authentication mode M10 in the case where the buckle 300 is opened and the push switch 340 is turned off.

In addition, when the buckle 300 is opened and the push switch 304 is turned off in the post-authentication mode M14, the control unit 400 causes the mode to transition to the pre-authentication mode M10 after elapse of a certain period of time.

Furthermore, in the case where a necessity to perform identity verification is caused by a software trigger after the transition from the authentication-in-progress mode M12 to the pre-authentication mode M10, the control unit 400 turns on the fingerprint sensor 302 and causes the mode to transition to the authentication-in-progress mode M12.

5. Method for Associating Fingerprint Sensor with Control Unit

Next, a method for associating the fingerprint sensor 302 with the control unit 400 is described. In the case where the users fingerprint information is stored in the microcomputer 302a of the fingerprint sensor 302, if the fingerprint sensor 302 is illicitly changed together with the microcomputer 302a, fingerprint authentication is performed on the basis of fingerprint information stored in the changed microcomputer 302a, and there is a possibility that fingerprint authentication by an unauthorized user succeeds. Therefore, when the control unit 400 receives an authentication success/failure signal from the fingerprint sensor 302, it is verified whether the signal has been transmitted from an authorized fingerprint sensor 302 with respect to the control unit 400. This makes it possible to avoid service from being provided on the basis of an authentication success/failure signal from an unauthorized fingerprint sensor 302 in the case where the control unit 400 is connected to the unauthorized fingerprint sensor 302.

Here, the fingerprint sensor 302 that owns a key K2 forming a pair with a key K1 owned by the control unit 400 is the authorized fingerprint sensor 302. Here, two methods are assumed as methods for defining and verifying the key K1 and the key K2 forming a pair. The first method is to use a pair of a public key and a secret key as the key K1 and the key K2. The control unit 400 performs public key authentication of challenge & response using a verification key (public key) as the key K1 and a signing key (secret key) as K2, thereby verifying that the fingerprint sensor 302 owns the key K2 corresponding to the key K1.

The second method is to use a common key as the key K1=the key K2. The control unit 400 performs common key authentication of challenge & response using a common key of a message authentication code (MAC) or a common key cipher (AES or the like) as the key K1=the key K2, thereby verifying that the fingerprint sensor 302 and the control unit 400 own the common key K1=key K2.

The following four methods can be assumed as methods for initial setting of the key K1 and the key K2. The first method is to set the key K1 and the key K2 in advance at the time of shipment from the factory. The second method is to share the common key K1=K2 by a technique such as DH key sharing at the time of initial setting of the electronic apparatus 1000 (only in the case of a common key).

The third method is a method in which the control unit 400 generates the key K1 and the key K2, and transmits the key K2 to the fingerprint sensor 302 to set the key K2. The fourth method is a method in which the fingerprint sensor 302 generates the key K1 and the key K2, and transmits the key K1 to the microcomputer 302a of the fingerprint sensor 302 to set the key K1.

However, in the case of the fourth method, if any key K1 is settable in the microcomputer 302a at any time, there is a possibility that the key K1 is set (rewritten) by an "unauthorized" fingerprint sensor. Therefore, for example, it is desirable to prevent the key K1 set in the microcomputer 302a from being rewritten, by, for example, accepting setting of the key K1 only in the case Where the key K1 is not set yet in the microcomputer 302a, but disabling rewriting of the key K1 in the case where the key K1 is already set.

Note that the belt 200 is often a leather belt or the like, as with watches, and the control unit 400 and the fingerprint sensor 302 cannot be connected by wire in some cases, for reasons of design. In that case, the control unit 400 and the fingerprint sensor 302 communicate by short-range wireless communication such as NFC, Bluetooth (registered trademark), or TransferJet; in such a case, association between the fingerprint sensor 302 and the control unit 400 is of particularly high importance, because hurdles for attack from a third party are lowered. Therefore, the association using the keys described above is preferably performed.

Figure 9:
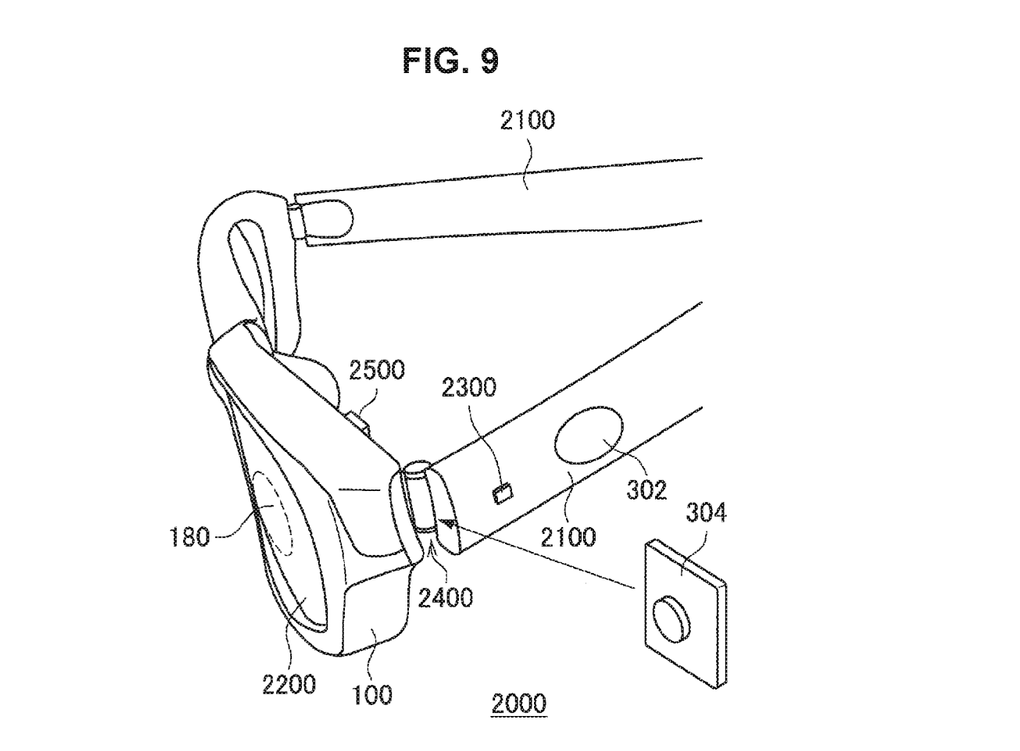
FIG. 9 is a schematic diagram illustrating another mode of the present embodiment.

As described above, according to the present embodiment, the fingerprint sensor 302 is provided on the buckle 300 of the electronic apparatus 1000 of a watch type that is worn by the user, and the push switch 304 brings the fingerprint sensor 304 into an on state in the case where the buckle is closed. This eliminates the need to always perform fingerprint sensing; thus, power consumption can be significantly reduced. In addition, the fingerprint sensor 302 is disposed at a position of the buckle 300 that is pressed by a finger when the buckle 300 is fastened; thus, fingerprint authentication can be performed at the same time as the buckle 300 is closed. Furthermore, since the fingerprint sensor 302 is disposed on the back surface of the buckle 300, unevenness due to the fingerprint sensor 302 can be avoided from being formed on the front surface of the main body 100, which can significantly improve design flexibility, 6. Example of Application to Glasses-Type Device FIG. 9 is a schematic diagram illustrating another mode of the present embodiment. The example illustrated in FIG. 9 is an example of application to a glasses-type device 2000. The glasses-type device 2000 is configured as a head mounted display (HMD), and includes the main body 100, the display unit 180, a hinge 2100, a lens 2200, and an operation input unit (operation switch) 2300. As with the electronic apparatus 1000 described above, the user can use service such as e-mail, SNS, electronic cash, a key function such as Smart Lock, and Wi-Fi/4G via the glasses-type device 2000.

The display unit 180 is provided in a portion of the lens 2200 of the glasses-type device 2000, and can display an image of text, a figure, or the like while keeping a transparent or semitransparent state, thereby displaying and superimposing a virtual object (GUI) of AR on scenery of a real space. That is, the glasses-type device 2000 is a see-through head mounted display (HMD). Note that the glasses-type device 2000 need not be of a see-through type. That is, the display unit 180 may be provided separately from the lens 2200 to provide an image to the user's pupil.

As illustrated in FIG. 9, the fingerprint sensor 302 is disposed on a temple 2100 of the glasses-type device 2000. The fingerprint sensor 302 can be disposed on the outside or the inside of the temple 2100.

The push switch 304 is disposed on a hinge 2400 of the glasses-type device 2000. When the user opens the temple 2100 to wear the glasses-type device 2000 on the face, the push switch 204 enters an on state. Thus, the mode transitions from the pre-authentication mode M10 to the authentication-in-progress mode M12, and the fingerprint sensor 302 enters an on state.

Figure 10:
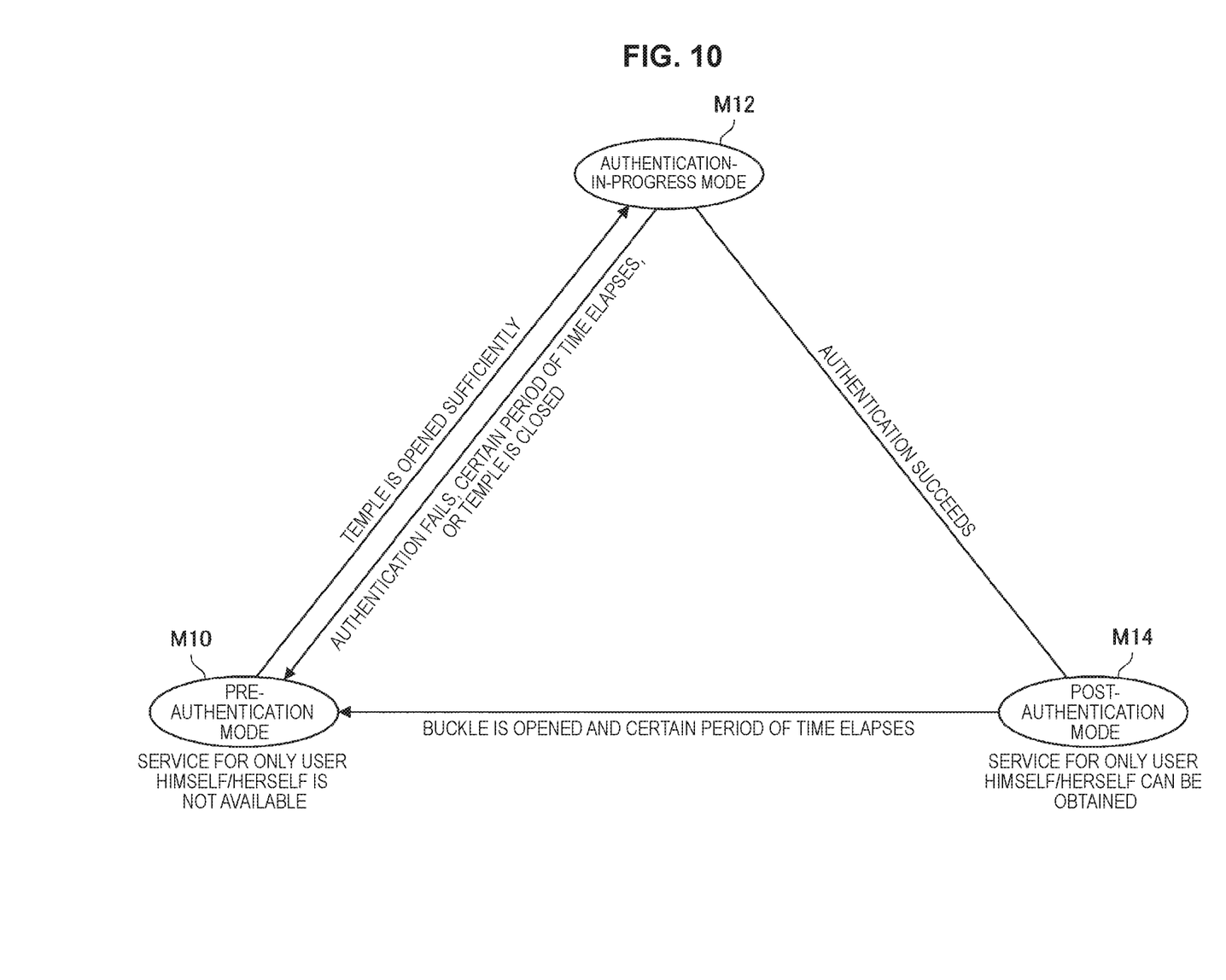
FIG. 10 is a schematic diagram illustrating an authentication mode of a glasses-type device.

Also in the glasses-type device 2000 configured as described above, mode transition similar to that in FIG. 4 is performed in accordance with a state of the push switch 304. FIG. 10 is a schematic diagram illustrating an authentication mode of the glasses-type device 2000. Mode transition is performed on the basis of an on/off state of the push switch 304 corresponding to operation of the buckle 300 in FIG. 4, whereas mode transition is performed on the basis of an on/off state of the push switch 304 corresponding to operation of the temple 2100 in FIG. 10. Other processing is similar to that in FIG. 4.

With the configuration illustrated in FIGS. 9 and 10, when the user tries to wear the glasses-type device 2000 on the face by opening the temple 2100, the fingerprint sensor 302 enters an on state and fingerprint authentication is performed. At this time, by providing the fingerprint sensor 302 at a place of the temple 2100 that the user holds with a finger when opening the temple 2100, fingerprint authentication can be performed at the same time as the temple 2100 is opened. Thus, fingerprint sensing can be started at the timing when the temple 2100 is opened sufficiently.

In addition, a sensor that acquires other biometric information of the user may be provided instead of the fingerprint sensor 302. For example, as illustrated in FIG. 9, a sensor 2500 that detects an iris of the user's eye may be provided, and iris authentication utilizing iris sensing may be performed. In this case, the user's iris information is held in advance in the control unit 400 or a microcomputer of the sensor 2500, and authentication is performed by comparing information of the user's iris acquired by the sensor 2500 at the time of authentication with the iris information held in advance. Examples of the sensor 2500 that performs iris sensing include an image sensor such as a CCD or a CMOS. To facilitate imaging of the iris, the sensor 2500 that performs iris sensing may be disposed inwardly on a rim or a bridge. In addition, illumination may be applied to the eye by an LED that applies near infrared light.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An electronic apparatus including:

a wearable part movable to be worn on a user's body; and a biometric information acquisition unit provided on the wearable part and configured to acquire biometric information of the user for user authentication.

(2)

The electronic apparatus according to (1), including a detection unit configured to detect movement of the wearable part, in which the biometric information acquisition unit acquires the biometric information when the detection unit detects that the wearable part is worn on the user's body.

(3)

The electronic apparatus according to (2) or (2), including a control unit configured to perform processing related to authentication based on the biometric information when the detection unit detects that the wearable part is worn on the user's body.

(4)

The electronic apparatus according to any one of (1) to (3), in which the control unit brings the biometric information acquisition unit into an on state when the detection unit detects that the wearable part is worn on the user's body.

(5)

The electronic apparatus according to (3) or (4), in which the control unit provides predetermined service to the user when the authentication based on the biometric information succeeds.

(6)

The electronic apparatus according to any one of (3) to (5), in which the control unit brings the biometric information acquisition unit into an off state when the authentication based on the biometric information succeeds.

(7)

The electronic apparatus according to any one of (3) to (6), in which the control unit brings the biometric information acquisition unit into an off state in a case where the authentication based on the biometric information fails, in a case where a certain period of time elapses without the authentication based on the biometric information succeeding, or in a case where the detection unit detects that the wearable part is detached from the user's body.

(8)

The electronic apparatus according to any one of (3) to (7), in which the control unit cancels the authentication and returns a mode to a mode before authentication in a case where the detection unit detects that the wearable part is detached from the user's body after the authentication based on the biometric information succeeds.

(9)

The electronic apparatus according to any one of (3) to (8), in which the biometric information acquisition unit performs the authentication based on the biometric information by comparing the biometric information acquired from the user with biometric information data held in advance, and after the authentication based on the biometric information succeeds, the control unit verifies whether or not the biometric information acquisition unit and the control unit own keys corresponding to each other in order to verify whether or not the biometric information acquisition unit has performed authentication on a basis of authorized biometric information data.

(10)

The electronic apparatus according to any one of (3) to (8), in which the biometric information acquisition unit performs the authentication based on the biometric information by comparing the biometric information acquired from the user with biometric information data, held in advance, and after the authentication based on the biometric information succeeds, the control unit verifies whether or not the biometric information acquisition unit and the control unit own a common key in order to verify whether or not the biometric information acquisition unit has performed authentication on a basis of authorized biometric information data.

(11)

The electronic apparatus according to any one of (1) to (10), in which the electronic apparatus is a watch-type apparatus.

(121)

The electronic apparatus according to (11), in which the wearable part is a buckle configured to be worn on an arm of the user by opening/closing operation.

(13)

The electronic apparatus according to (11), in which the wearable part is a belt configured to be worn on or detached from an arm of the user by sliding.

(14)

The electronic apparatus according to any one of (1) to (13), in which the biometric information acquisition unit acquires fingerprint information of the user as the biometric information.

(15)

The electronic apparatus according to any one of (1) to (13), in which the biometric information acquisition unit acquires information regarding a vein of a hand of the user as the biometric information.

(16)

An electronic apparatus including:

a wearable part movable to be worn on or detached from a user's body;

a biometric information acquisition unit configured to acquire biometric information of the user for user authentication; and a detection unit configured to detect movement of the wearable part, in which the biometric information acquisition unit acquires the biometric information when the detection unit detects that the wearable part is worn on the user's body.

(17)

The electronic apparatus according to (16), in which the biometric information acquisition unit acquires iris information of the user as the biometric information.

(18)

An authentication method including:

detecting movement of a wearable part movable for an electronic apparatus to be worn on a user's body; and acquiring biometric information of the user in order to perform authentication on a basis of the biometric information when the movement of the wearable part is detected.

(19)

A program causing a computer to function as:

means for detecting movement of a wearable part movable for an electronic apparatus to be worn on a user's body; and means for acquiring biometric information of the user in order to perform authentication on a basis of the biometric information when the movement of the wearable part is detected.

REFERENCE SIGNS LIST

1000 electronic apparatus
300 buckle
302 fingerprint sensor
304 push switch
400 control unit

The invention claimed is:

1. An electronic apparatus comprising:

a wearable part movable to be worn on a user's body;

a biometric information acquisition unit provided on the wearable part and configured to acquire biometric information of the user for user authentication;

a detection unit configured to detect movement of the wearable part; and a control unit configured to perform processing related to authentication based on the biometric information when the detection unit detects that the wearable part is worn on the user's body, wherein the biometric information acquisition unit acquires the biometric information when the detection unit detects that the wearable part is worn on the user's body, wherein the biometric information acquisition unit performs the authentication based on the biometric information by comparing the biometric information acquired from the user with biometric information data held in advance, wherein after the authentication based on the biometric information succeeds, the control unit verifies whether or not the biometric information acquisition unit and the control unit own keys corresponding to each other in order to verify whether or not the biometric information acquisition unit has performed authentication on a basis of authorized biometric information data, and wherein the biometric information acquisition unit is implemented via at least one biometric sensor, wherein the detection unit is implemented via at least one of a switch or a sensor, and wherein the control unit is implemented via at least one processor.

2. The electronic apparatus according to claim 1, wherein the control unit brings the biometric information acquisition unit into an on state when the detection unit detects that the wearable part is worn on the user's body.

3. The electronic apparatus according to claim 1, wherein the control unit provides predetermined service to the user when the authentication based on the biometric information succeeds.

4. The electronic apparatus according to claim 1, wherein the control unit brings the biometric information acquisition unit into an off state when the authentication based on the biometric information succeeds.

5. The electronic apparatus according to claim 1, wherein the control unit brings the biometric information acquisition unit into an off state in a case where the authentication based on the biometric information fails, in a case where a certain period of time elapses without the authentication based on the biometric information succeeding, or in a case where the detection unit detects that the wearable part is detached from the user's body.

6. The electronic apparatus according to claim 1, wherein the control unit cancels the authentication and returns a mode to a mode before authentication in a case where the detection unit detects that the wearable part is detached from the user's body after the authentication based on the biometric information succeeds.

7. The electronic apparatus according to claim 1, wherein after the authentication based on the biometric information succeeds, the control unit verifies whether or not the biometric information acquisition unit and the control unit own a common key in order to verify whether or not the biometric information acquisition unit has performed authentication on a basis of authorized biometric information data.

8. The electronic apparatus according to claim 1, wherein the electronic apparatus is a watch-type apparatus.

9. The electronic apparatus according to claim 8, wherein the wearable part is a buckle configured to be worn on an arm of the user by opening/closing operation.

10. The electronic apparatus according to claim 8, wherein the wearable part is a belt configured to be worn on or detached from an arm of the user by sliding.

11. The electronic apparatus according to claim 1, wherein the biometric information acquisition unit acquires fingerprint information of the user as the biometric information.

12. The electronic apparatus according to claim 1, wherein the biometric information acquisition unit acquires information regarding a vein of a hand of the user as the biometric information.

13. An electronic apparatus comprising:
a wearable part movable to be worn on or detached from a user's body;
a biometric information acquisition unit configured to acquire biometric information of the user for user authentication;
a detection unit configured to detect movement of the wearable part; and
a control unit configured to perform processing related to authentication based on the biometric information when the detection unit detects that the wearable part is worn on the user's body,
wherein the biometric information acquisition unit acquires the biometric information when the detection unit detects that the wearable part is worn on the user's body,
wherein the biometric information acquisition unit performs the authentication based on the biometric information by comparing the biometric information acquired from the user with biometric information data held in advance,
wherein after the authentication based on the biometric information succeeds, the control unit verifies whether or not the biometric information acquisition unit and the control unit own keys corresponding to each other in order to verify whether or not the biometric information acquisition unit has performed authentication on a basis of authorized biometric information data, and
wherein the biometric information acquisition unit is implemented via at least one biometric sensor,
wherein the detection unit is implemented via at least one of a switch or a sensor, and
wherein the control unit is implemented via at least one processor.

14. The electronic apparatus according to claim 13, wherein the biometric information acquisition unit acquires iris information of the user as the biometric information.

15. An authentication method comprising:
detecting movement of a wearable part movable for an electronic apparatus to be worn on a user's body;
acquiring biometric information of the user in order to perform authentication on a basis of the biometric information when the movement of the wearable part is detected;
detecting movement of the wearable part; and
performing processing related to authentication based on the biometric information when it is detected that the wearable part is worn on the user's body,
wherein the biometric information is acquired when the detection unit detects that the wearable part is worn on the user's body,
wherein the authentication is performed based on the biometric information by comparing the biometric information acquired from the user with biometric information data held in advance, and
wherein after the authentication based on the biometric information succeeds, it is verified whether or not keys correspond to each other in order to verify whether or not authentication has been performed on a basis of authorized biometric information data.

16. A non-transitory computer-readable storage medium having embodied thereon a program, which when executed by a computer causes the computer to execute a method, the method comprising:
detecting movement of a wearable part movable for an electronic apparatus to be worn on a user's body;
acquiring biometric information of the user in order to perform authentication on a basis of the biometric information when the movement of the wearable part is detected;
detecting movement of the wearable part; and performing processing related to authentication based on the biometric information when it is detected that the wearable part is worn on the user's body, wherein the biometric information is acquired when the detection unit detects that the wearable part is worn on the user's body, wherein the authentication is performed based on the biometric information by comparing the biometric information acquired from the user with biometric information data held in advance, and wherein after the authentication based on the biometric information succeeds, it is verified whether or not keys correspond to each other in order to verify whether or not authentication has been performed on a basis of authorized biometric information data.

* * * * *